United States Patent [19]

Sainomoto et al.

[11] Patent Number: 4,592,366

[45] Date of Patent: Jun. 3, 1986

[54] AUTOMATED BLOOD PRESSURE MONITORING INSTRUMENT

[75] Inventors: Yoshinori Sainomoto, Ikeda; Fumio Kitagawa, Neyagawa, both of Japan

[73] Assignee: Matsushita Electric Works, Ltd., Osaka, Japan

[21] Appl. No.: 600,413

[22] Filed: Apr. 16, 1984

[51] Int. Cl.$^4$ .............................................. A61B 5/02
[52] U.S. Cl. .................................. 128/680; 128/715
[58] Field of Search ................ 128/672, 677, 680–683, 128/715, 773; 181/131

[56] References Cited

U.S. PATENT DOCUMENTS

| | | | |
|---|---|---|---|
| 3,762,397 | 10/1973 | Cage | 128/715 X |
| 3,878,834 | 4/1975 | Sanderson | 128/680 |
| 3,999,625 | 12/1976 | Pickett et al. | 128/715 X |
| 4,154,238 | 5/1979 | Link | 128/681 |
| 4,313,445 | 2/1982 | Georgi | 128/682 X |
| 4,469,107 | 9/1984 | Asmar et al. | 128/681 |
| 4,475,557 | 10/1984 | Hatschek et al. | 128/680 X |
| 4,476,876 | 10/1984 | Uchiyama | 128/682 |

FOREIGN PATENT DOCUMENTS

| | | | |
|---|---|---|---|
| 8401499 | 4/1984 | PCT Int'l Appl. | 128/680 |
| 2087238 | 2/1982 | United Kingdom | 128/680 |
| 0976951 | 11/1982 | U.S.S.R. | 128/680 |

Primary Examiner—Kyle L. Howell
Assistant Examiner—Angela D. Sykes
Attorney, Agent, or Firm—Stevens, Davis, Miller & Mosher

[57] ABSTRACT

An automated blood pressure monitoring instrument including a noise level detector which enables the instrument to have the sound sensing performance analogous to the human ear. Sounds, including Korotkoff sounds, emitted from the occluded artery of a subject person are transduced into corresponding electric signals to be fed through a filter to the said noise level detector. At the noise level detector, a noise level is calculated from the incoming signals in such a manner as to exclude from this calculation values of expected Korotkoff sound levels and the like which are normally thought to be much higher than an estimated or assumed level of noises associated with the body in the normal blood pressure measurement. The noise level thus detected will vary depending upon the conditions of a subject person as well as varies from person to person, and therefore acts as an effective reference for identifying the Korotkoff sounds. Also included in the instrument is a comparator which discriminates the Korotkoff sounds from the incoming sounds by comparison of their sound levels with a Korotkoff sound reference level which is proportional to said noise level and is naturally a variable level characteristic to the conditions of the subject person. This enables the instrument to discern the differences in the incoming sound signals as the human ear might, thus providing an accurate and effective measurement. When the comparator judges that the incoming sound signals have the level exceeding the above Korotkoff sound reference level, it generates a Korotkoff sound signal representative of the Korotkoff sound. A display is included in the instrument for responding to the appearance and disappearance of the Korotkoff sound signal for providing systolic and diastolic blood pressure indications respectively.

11 Claims, 15 Drawing Figures

AUTOMATED BLOOD PRESSURE MONITORING INSTRUMENT

BACKGROUND OF THE DISCLOSURE

1. Fields of the Invention

This invention is directed to an automated blood pressure monitoring instrument, more particularly to a non-invasive detection instrument for automatically measuring arterial blood pressures by an indirect auscultation technique.

2. Description of the Prior Art

There have been provided a wide variety of blood pressure measuring instruments based on listening for the Korotkoff sounds. The common technique with the use of such instrument is to place an inflatable cuff around the arm of a user and to occlude the artery in the arm by increasing the pressure within the cuff above an expected systolic pressure by about 20 to 30 mmHg. Thereafter, the pressure in the cuff is allowed to bleed down slowly at a ratio of about 2 to 3 mmHg/sec for detecting the Korotkoff sounds by means of a pressure transducer such as a microphone or the like. The pressures in the cuff at the time of the appearance and disappearance is then recognized by the instrument to be the indications of the systolic and diastolic pressures. However, such prior art instruments have long suffered problems that the detection by the instruments is not always in exact coincidence with the detection by doctors or the like personnel who have been acquainted with the blood pressure measurement using a conventional stethoscope together with a mercury manometer and that detection based upon the human ear has long been widely established and recognized as the standard reference for indicating the systolic and diastolic pressures. There is an inability for the artificial sound sensing means to automatically adjust a critical level, while such automatic critical level adjusting ability is inherent to the human ear and is most reliable for recognizing incoming sounds of important intensity by relative comparison thereof with the self-adjusting critical level in such a way as not to be substantially affected by possible noises. In other words, the human ear has the filtering function for a target sound in such a manner as to ignore possible noises, thus recognizing the target sound as having a larger level difference between the target and noises than actually exists. This lack in self adjusting ability of the critical level may also be the cause of mistaking the noises for the Korotkoff sounds when the noise is larger and therefore may result in erroneous blood pressure measurements. In fact, there has never been provided a blood pressure monitoring instrument capable of automatically adjusting its critical level depending upon a level of noises inevitably emanated from the occluded artery and/or the body during the measurement. Accordingly, it is most desirable to present an automated blood pressure monitoring instrument capable of ignoring the noises so as to provide an accurate measurement approximating the measurement by skilled personnel.

In addition, the above inconsistency between the blood pressure measurement by the prior art automated instrument and by the human ear can be reasonable explained also in terms of the fact that the skilled personnel rely on a conventional stethoscope to listen for the Korotkoff sounds while the automated instrument receives the Korotkoff sounds through the sound sensing means such as the microphone placed rather directly on a suitable portion of the body. Therefore, this structural difference with respect to the sound conducting path should be taken into account for approximating the measurement by the automated instrument to that by the auscultation technique with the conventional stethoscope. In connection with the above, a particular attention should be directed to the difference in frequency response between the artificial sound sensing means employed and the human ear for obtaining the measurement results as close as those by the skilled personnel.

In the meanwhile, the Korotkoff sounds upon which both the automated instrument and the human ear rely for determining the systolic and diastolic blood pressures have been analyzed by Swan to exhibit a unique spectrum during the blood pressure measurement. That is, the spectrum of the Korotkoff sounds is found to have five remarkable points $S_1$ to $S_5$ and four corresponding phases I, II, II, IV between the adjacent points, $S_1$ being defined to be indicative of the systolic pressure and $S_5$ or $S_4$ indicative of the diastolic pressure. Such unique spectrum of the Korotkoff sounds has been practically found to successively appear in correct or proper measuring procedure, thus constituting a standard for determining whether or not the measurement is being properly performed. Particularly worthy of mention among the characteristics of this spectrum is the appearance of a voiced tone associated with a particular Korotkoff sound, or the Korotkoff sound in the second phase $S_2$. This can be an easy but strong standard for the judgement of the effectiveness of the measurement. The voiced tone is found to appear immediately after the peak of the Korotkoff sound in the second phase $S_2$ if the measurement is being properly performed. In fact, the condition in which said voiced tone appears takes the advantage of producing the Korotkoff sounds of a greater sound pressure than at the condition in which the voiced tone fails to appear, thus giving an increased S/N ratio for easy and accurate measurement. It is of course within the recognition of the above skilled personnel to listen for this voiced tone for determining their measuring procedure to be effective or not. Accordingly, it is strongly desired for the automated measuring instrument to discriminate the voiced tone associated with the particular Korotkoff sound in view of determining the effectiveness of its measurement.

SUMMARY OF THE INVENTION

The above disadvantages and problems have been obviated by the present invention which is aimed to present an automated blood pressure measurement as closely as that made by a skilled person such as a doctor, nurse or the like who relies upon one's ear by the help of a conventional stethoscope. The automated blood pressure monitoring instrument of the present invention comprises means for externally occluding an artery with pressure in combination with transducer means responding to sounds including Korotkoff sounds emitted from the occluded artery for generating electric signals representative thereof. Band pass filter means receives the output from the transducer means to allow only the output having a frequency range in the vicinity of the frequencies inherent to the Korotkoff sounds to pass. Advantageously included in the instrument is noise level detecting means which receives the output from the band pass filter means to calculate a noise level therefrom in such a manner as to exclude from this calculation valuts of expected Korotkoff sound levels and the like which are normally thought to be much higher than an estimated or assumed level of noises emanated from the occluded artery and the body in the normal course of blood pressure measurements. The noise level thus detected varies depending upon the conditions of a subject person as well as varies from person to person, and therefore acts as an effective standard for identifying the Korotkoff sounds of which level is known to be higher than the varying noise level. To this end, comparator means is introduced to discriminate the Korotkoff sounds from the incoming sounds from the band pass filter by comparison of their sound levels with a Korotkoff sound reference level which is proportional to said noise level and is above the noise level, whereby when the former exceeds the latter the comparator means generates a Korotkoff sound signal representative of the Korotkoff sound. Also included in the instrument is display means which responds to the appearance and disappearance of the Korotkoff sound signal for providing systolic and diastolic blood pressure indications respectively. With this arrangement of automatically setting a noise level and the Korotkoff sound reference level which differ depending upon the conditions of the subject person and from person to person, the instrument can successfully discern the Korotkoff sounds from the associated artifact noises within the body of the subject person.

Accordingly, it is a primary object of the present invention to provide an automated blood pressure monitoring instrument capable of effectively identifying the Korotkoff sounds without being disturbed by the artifact noises and therefore providing an accurate measurement.

Said transducer means comprises a conventional stethoscope with a pressure sensing pad adapted in use to be placed on the human body adjacent to the occluded artery and a microphone mounted within an ear plug of the stethoscope. Connected to the microphone is a microphone sensitivity compensating filter for providing a generally flat frequency response. A frequency weighting filter is also incorporated for adjusting the output from the microphone sensitivity compensating filter to an equal loudness contour which is characteristic to the human. This enables the automated measurement to approximate that performed by the skilled person such as the doctor and the like, providing the measurement results as closely as those obtained by such skilled person and widely recognized to be available. For this purpose, it is preferred that said frequency weighting filter have a reverse characteristic of the 60-phon equal loudness contours (defined as ISO/R226) such that the output of frequency weighting filter provides a frequency characteristic approximating that loudness contours.

Therefore, it is another object of the present invention to provide an automated blood pressure monitoring instrument which presents a Korotkoff sound sensing technique or method close to that of a skilled person's ear, thus providing effective measuring results in the sense of being well coincident with the generally accepted blood pressure measuring results obtainable by doctors and the like skiled personnel.

In a preferred embodiment, there is disclosed a unique and advantageous modification of the stethoscope which is of conventional type and is equipped with the microphone. By this modification, the microphone can have an acoustic characteristic very similar to that of the human ear so as to provide effective and accurate measuring results, which is a further object of the present invention.

In addition to the above useful features, the present invention discloses a still other important advantageous feature to detect the appearance of a voiced tone associated with a particular Korotkoff sound during the measurement for determining whether or not the measured results is effective. The analysis of such voiced tone proves that it results from the minor successive signals appearing for a certain time period subsequent to the Korotkoff sound in the second phase as shown in the spectrum of the Korotkoff sound proposed by Swan. But unfortunately, the level of these minor signals responsible for the voiced tone is not so large as that of the Korotkoff sounds and therefore is difficult to be detected by comparison with said Korotkoff sound reference level. To overcome this shortcoming, the present invention provides a novel arrangement of a voice tone identifying circuit for discriminating the voiced tone in question in view of the fact that there should be present signals of less but detectable level during a certain time interval after the appearance of the particular Korotkoff sound although the signals being of less level than the Korotkoff sound. Additionally, notifying means is incorporated so as to notify the user of whether the voiced tone is acknowledged as a critical standard for judging whether or not the on-going measurement is being correctly performed. Based on the above acknowledgement, the voiced tone identifying circuit is designed to include first comparator means for comparison of the level of the output from the band pass filter means with a first predetermined reference level higher than said noise level in order to judge whether or not the incoming signals include the Korotkoff sounds which may be accompanied by the voiced tone. When the incoming signals exceed that first reference level or when the Korotkoff sounds possibly accompanied by the voiced tone is acknowledged, the first comparator means will issue a monitoring signal for defining a predetermined time period beginning after a preselected time interval from the appearance of such Korotkoff sound. Cooperating with the first comparator means is recognition means which produces a recognition signal when it recognizes during a predetermined time period defined by the above monitoring signal that the level of the output from the band pass filter means is above a second predetermined reference level. Said predetermined time period is set to cover the time period during which the voiced tone is expected to appear subsequent to the associated Korotkoff sound, and the second reference level is set to be above said noise level but below said Korotkoff sound reference level so as to be a suitable value (voiced tone reference level) for discriminating the voiced tone. That is, the recognition means has the function of monitoring whether or not the incoming signal has a signal level exceeding the noise level within the time period in which the voiced tone is expected to appear, so that it can identify the appearance of the voiced tone and issues a recognition signal upon the appearance of the voice tone. Such recognition signal therefore is representative of the voiced tone which appears subsequent to the associated Korotkoff sound and is utilized to actuate the above notifying means, informing the user of whether or not the measuring operation is being properly performed.

Accordingly, it is a still further object of the present invention to provide an automated blood pressure monitoring instrument which can evaluate by itself the effectiveness of its measuring operation.

In the present invention, there are disclosed more concrete constructions of said voiced tone identifying circuit of advantageous features. These and other object and advantages will be apparent from the following detailed description of one preferred embodiment with reference to the accompanying drawings.

DETAILED DESCRIPTION OF THE PREFERRED EMBODIMENT

Figure 1:
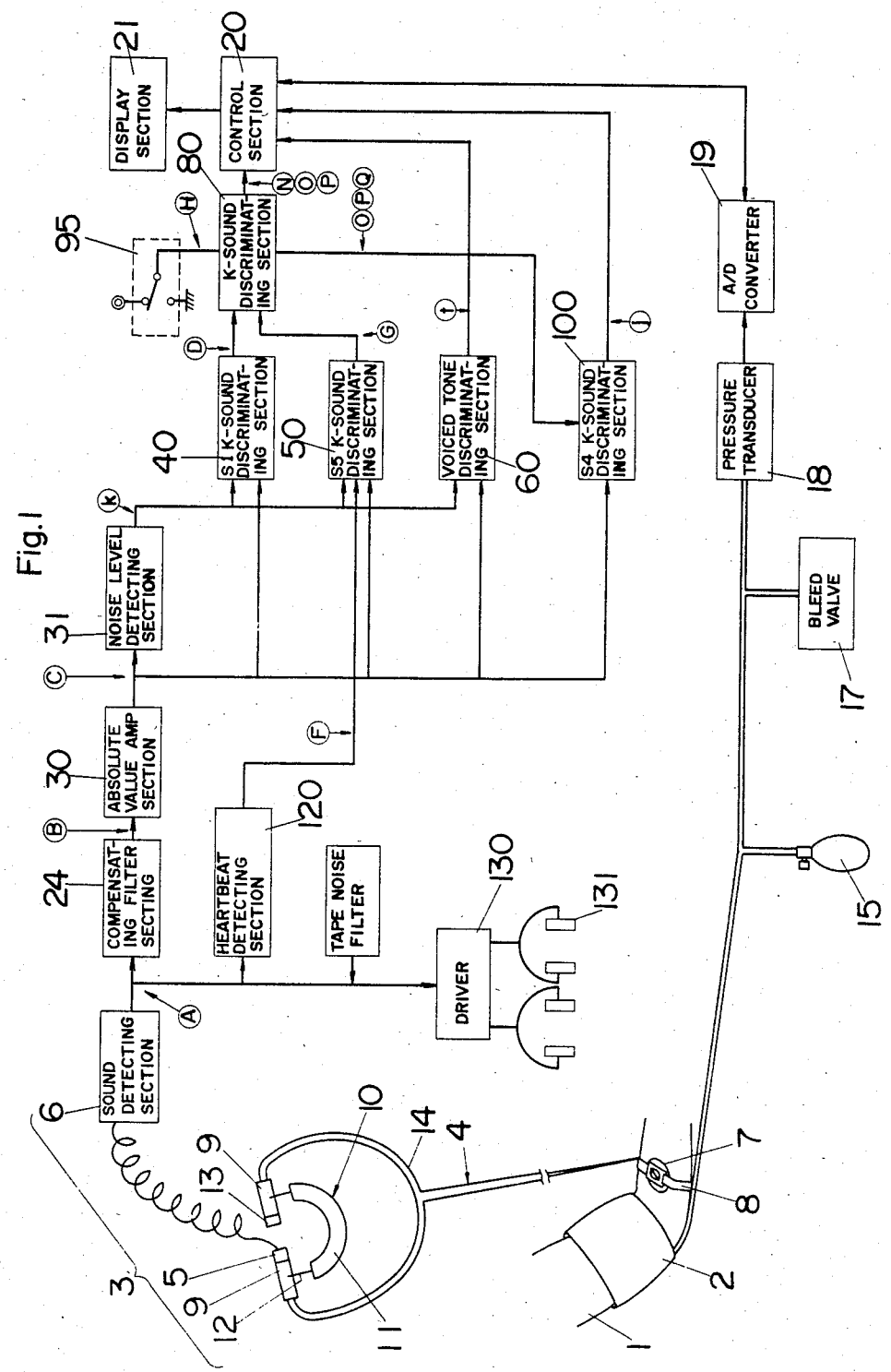
FIG. 1 is a block diagram schematically illustrating an automated blood pressure monitoring instrument in accordance with a preferred embodiment of the present invention.
Figure 2:
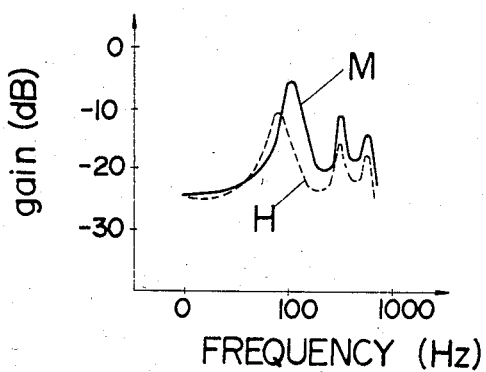
FIG. 2 is a chart showing the frequency-response characteristic to the human ear when using a conventional stethoscope in comparison with that of a microphone when incorporated in one ear plug of the same stethoscope.

Referring firstly to FIG. 1, there is illustrated a functional block diagram of a blood pressure monitoring instrument in accordance with a preferred embodiment of the present invention. The instrument comprises an inflatable bag 2 to be wrapped around the upper arm 1 of a user for occluding the artery in the upper arm 1 and transducer means 3 responding to sounds including Korotkoff sounds emitted from the occluded artery for generating electric signals representative thereof. Said transducer means 3 is basically composed of a stethoscope 4 incorporated therein a microphone 5 and sound detecting section 6 including a driver circuit for the microphone 5 which is in this embodiment a capacitor microphone the sensitivity of which is specified as 0 $dB = 1$ V/$\mu$bar. The stethoscope 4 is constructed as a modified one of a conventional stethoscope (sold under the trade name of Littmann) which comprises a sensing pad 7 to be placed on a part of the body by means of fastening means 8 and a Y-shaped tubing 14 the bifurcated branches of which have ear plugs at their respective end portions. The above modification resides in the addition of extension tubes 9 each having a length of about 30 mm, generally the same length as the external auditory canal of the human ear, to be connected respectively to the ear plugs. Another modification resides in the addition of a bypass tube 10 interconnecting said extension tubes 9. Said bypass tube 10 is composed of a conducting tube 11 having a length of 135 mm and an inside diameter of 4 mm, and needles 12 extending from the both ends thereof, each needle 12 having a length of 50 mm and an inside diameter of 1.2 mm. The microphone 5 is mounted in one extension tube 9 in such a manner as to close the outer extremity thereof, while a dummy 13 likewise closes the other extension tube 9. In the present embodiment, the same microphone without electrical connection is utilized as the dummy 13, but other closures such as a cap or the life may be utilized. The bypass tube 10 thus constructed is incorporated in the stethoscope 4 with the needles 12 being inserted respectively to said extension tubes 9 for intercommunication therewith, rendering this stethoscope 4 with the microphone 5 to be analogous to the human ear. FIG. 2 shows a curve [H] with regard to the human ear on a graph of sound intensity in gains versus frequency as compared to a curve [M] with regard to the microphone when used with the stethoscope from which said extension tubes 9 and bypass tube 10 are removed. The above modification is introduced for adjusting the frequency characteristic of the microphone 5 to that of the human ear and thus enables the microphone 5 to listen for sounds in the same condition as the human ear might. It is noted at this point that the microphone 5 acknowledges the sounds in the waveform as indicated at (A) of FIG. 12, such sound inevitably including pulsating sounds due to the heartbeats. Said inflatable cuff 2 is in use to be inflated to a pressure value above an expected systolic blood pressure by about 20 to 30 mmHg by pumping up a squeeze bulb 15 connected through a tubing 16 to the inflatable cuff 2 for occluding the artery in the upper arm 1 of the user. Thereafter, the pressure in the cuff 2 is allowed to reduce gradually by opening a bleed valve 17 at a rate of 2 to 3 mmHg such that the microphone 5 can sense the sounds including Korotkoff sounds from the occluded artery under the condition ot the above sensing pad 7 being placed on the arm at a contacting pressure of 200 to 300 g/cm$^2$ at the portion about several centimeters spaced outwardly from the cuff 2. The continuously varying pressure within the cuff 2 is sensed by a pressure transducer 18 the corresponding output of which is then fed through an analog-digital converter 19 to a control section 20 where it is processed in a manner as described hereinafter to provide blood pressure indications on a digital display section 21.

Figure 3A:
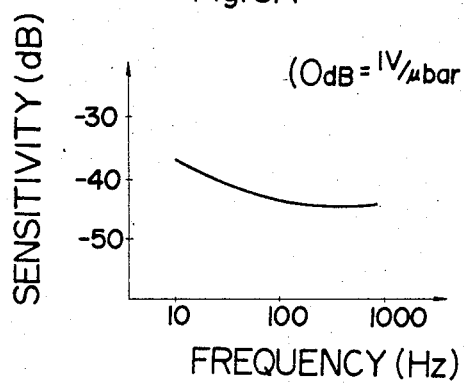
FIG. 3(A) is a chart showing the frequency-response curve of the microphone employed in the present invention.
Figure 3B:
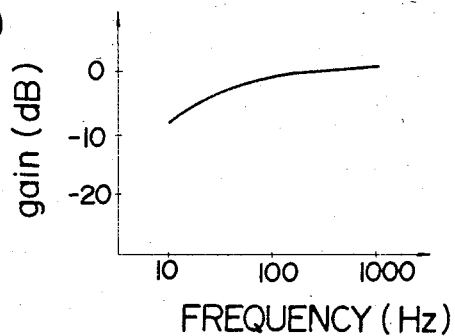
FIG. 3(B) is a chart showing the frequency-response curve of a microphone sensitivity compensating filter employed in combination with the above microphone.
Figure 4A:
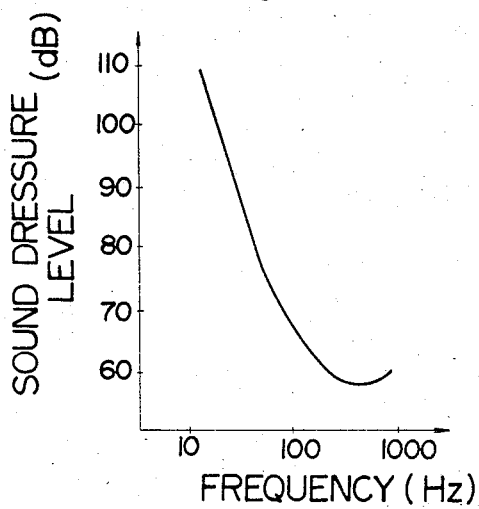
FIG. 4(A) is a chart showing the 60-phon equal loudness contour defined as ISO/R266.
Figure 4B:
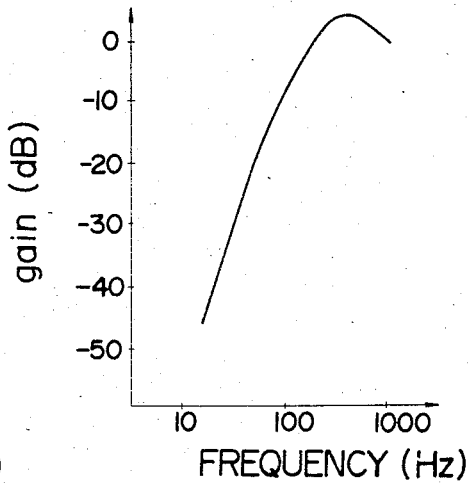
FIG. 4(B) is a chart showing frequency-response characteristic curve of a frequency weighting filter employed together with the above microphone sensitivity compensating filter.

A compensating filter section 24 receives the output A from said sound detecting section 6 as the amplified signal from the microphone 5 and operates for providing corresponding output signals suitable in the subsequent signal processing stages. The filter section 24 includes three different filters (not shown), one being a microphone sensitivity compensating filter for providing a generally flat response over an audio frequency range, another being a frequency weighting filter for adjusting the response to a suitable sound level at which the human ear could normally listen for the Kororkoff sounds, and the other being a band pass filter allowing signals within a frequency band ranging from 20 to 200 Hz to pass for selecting signals representative of the Korotkoff sounds and excluding the signals representative of the heartbeats. Since the microphone employed in this embodiment has the frequency response characteristic as shown in FIG. 3(A), the microphone sensitivity compensating filter having the reverse characteristic to that of the microphone as shown in FIG. 3(B) is necessary for providing an overall generally flat response. In the present embodiment, the frequency weighting filter is selected to have the frequency response in which the gain at 1000 Hz is selected to be 0 dB [FIG. 4(B)] and which is of reverse characteristic to the 60-phon equal loudness contour defined as ISO/R226 [FIG. 4(A)] so as to present an output signal indicated at B of FIG. 12 at generally the same sound level as the human ear could listen for the Korotkoff sounds in the normal blood pressure measuring condition. At this point, it should be noted that the study on the technique of conventional blood pressure measurement by doctors and like skilled personnel who rely upon their ear to discriminate the Korotkoff sounds has proved that they normally recognize the Korotkoff sounds at a level of about 60 dB, although it may differ to some extent depending upon the measuring conditions. This is the reason why the 60-phon equal loudness contour is taken into consideration in the present embodiment in order to adjust the auditory level of the microphone to the listening level of the human ear. In connection with the above, it is also to be noted that the human ear has an inherent advantageous feature of automatically changing its reference level in such a way as to clearly discriminate the Korotkoff sounds from artifact noise within the body without being disturbed by the resulting noise level. This advantageous feature is realized in the instrument of the present invention by adopting noise level detecting means, the details of which will be now described.

Figure 5:
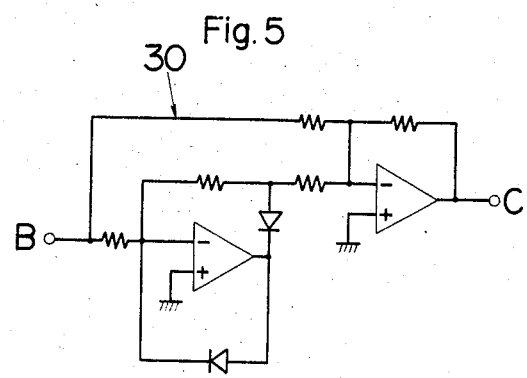
FIG. 5 is a circuit diagram showing an absolute value amplifier section employed in the above embodiment.
Figure 6:
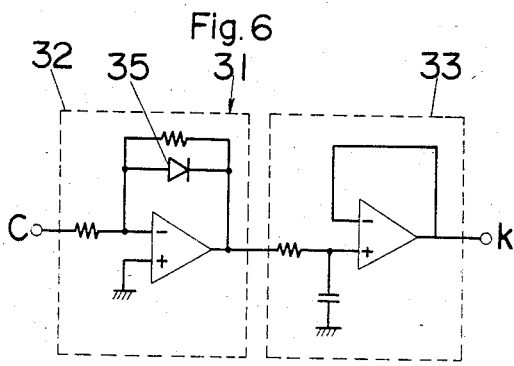
FIG. 6 is a circuit diagram showing a noise level detecting section in the above embodiment.

Said noise level detecting means comprises an absolute value amplifier section 30 and noise level detecting section 31. The output B from the filter section 24 is applied to the absolute value amplifier 30, the circuit arrangement of which is shown in FIG. 5. The amplifier 30 provides an analog signal C representative of the intensity of the incoming sound signals B. The signal C is then fed to the noise level detecting section 31 which comprises a clipper-limiter 32 and an averaging circuit 33, as shown in FIG. 6. The clipper-limiter 32 is designed to only receive the signals representative of artifact noises within the body while to reject other signals at such a higher level as to be representative of the Korotkoff sounds and other extraordinary sounds due to excessive arm motion for the purpose or sampling signals which are expected to result from the artifact noises within the body appearing in the normal blood pressure measuring condition. Considering that the noise level due to the artifact noises occurring unexceptionally in the normal course of blood pressure measuring is within a certain limit value which may vary depending on an individual difference but can be much lower than the level of the Korotkoff sounds and said extraordinary sounds, the above limit value adapted for the present arrangement is calculated in view of the above individual difference to be 0.6 V at the most. Therefore, diode 35 having a forward bias of 0.6 V is utilized in tne clipper-limiter 32 such that it provides an output which is a function of the input amplitude for the input value below said limit voltage of 0.6 V but remains at the peak value for the input value above 0.6 V. The output ot the clipper-limiter 32 is thereafter fed to the averaging circuit 33 to present a voltage signal (k) representative of an instantaneous noise level within the body in the blood pressure measurement. The signal (k) from the noise level detecting section 31 is then applied to a S-1 point Korotkoff sound discriminating section 40, to a S-5 point Korotkoff sound discriminating section 50 and to a voiced tone discriminating section 60. The above S-1 and S-5 points Korotkoff sounds and a S-4 point Korotkoff sound, which will be explained later, are found by Swan in his analysis of the Korotkoff sounds to be typical points appearing in the blood pressure measurement and has been widely recognized to correctly correspond to generally accepted or available blood pressure values indicating systolic and diastolic pressures. That is, the cuff pressure when S-1 point or first Korotkoff sound (hereinafter referred to as S1 K-sound) is heard is the indication of systolic pressure and tne cuff pressure when S-5 point i.e. the last Korotkoff sound (S5 K-sound) or S-4 point Korotkoff sound (S4 K-sound) is heard is the indication of diastolic pressure. The above confusion in expressing the diastolic pressure results from two different theories, one favoring S5 K-sound as correctly correspond to the diastolic pressure and the other favoring S4 K-sound. For this reason, it has been a usual practice to indicate both diastolic pressure values corresponding to S4 and S5 K-sound together with a systolic pressure value for S1 K-sound, for example, 142/82/78 mmHg as indicating in this order the pressure values for S1, S4 and S5 K-sounds.

Figure 7:
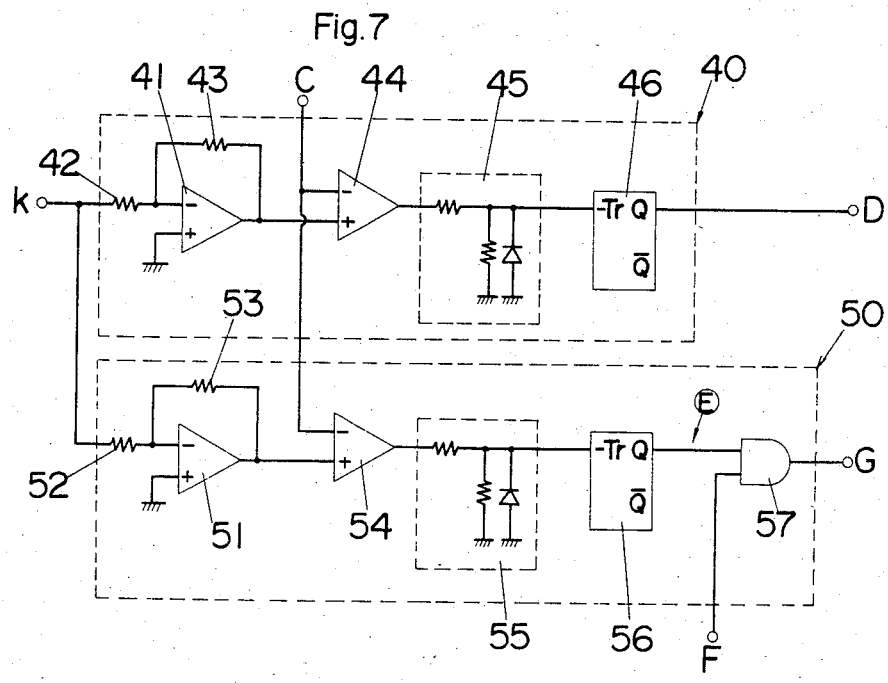
FIG. 7 is a circuit diagram showing a S1 and S5 Korotkoff sound discriminating sections employed in the above embodiment.

Referring back to FIG. 1 and further referring to FIG. 7, said S1 K-sound discriminating section 40 receives both signals C and (k) respectively from the absolute value amplifier section 30 and the noise level detecting section 31 so as to judge whether the microphone 5 senses a sound at such a greater level as to indicate the appearance of the Korotkoff sound. The discrimination of the first Korotkoff sound or S1 K-sound can be made in a cooperative manner with a subsequent K-sound evaluating section 80. Included in said S1 K-sound discriminating section 40 is an operational amplifier 41 constituting in combination with resistors 42 and 43 of different values a constant-gain multiplier which responds to the input signal (k) from said noise level detecring section 31 for providing a S1 K-sound reference voltage level used for comparison to identify the sound at the above level suggesting the appearance of the Korotkoff sound. Such S1 K-sound reference voltage level is of course set to be above said noise level for use to discriminate first or S1 K-sound and is therefore referred hereinafter referred to as S1 K-sound reference level. That is, the S1 K-sound reference level in the present embodiment is adjusted by choosing suitable values for the resistors 42 and 43 so as to be equivalent to the listening level at which the human ear could discriminate the Korotkoff sounds while suffering artifact noises within the body, for example, to be approximately 60 dB in consideratio of a normally expected noise level, although it automatically varies with varying noise level. The output of the operational amplifier 41 or said S1 K-sound reference level is applied to a comparator 44 together with the signal C from said absolute amplifier 30 to be compared therewith in such a way that when the the level of signal C exceeds the S1 K-sound reference level the comparator 44 provides a high level output voltage. At this occurrence, a multivibrator 46 receives that high level output voltage from the comparator 44 through a voltage adjusting circuit 45 to issue a gate signal indicating at D of FIG. 12, such gate signal D having a pulse width of 10 msec and being applied to the K-sound evaluating section 80 for the purpose of judging whether the input signal C of a greater level enough to actuate the monostable multivibrator 46 results from the Korotkoff sound or from a simple noise having a level equivalent to the Korotkoff sound, the details of which will be explained later.

Also shown in FIG. 7 is said S-5 joint Korotkoff sound discriminating section 50 which includes an operational amplifier 51 constituting together with a pair of resistors 52 and 53 of different values a similar constant-gain multiplier as employed in the above S1 K-sound discriminating section 40 but providing in response to the same input signal (k) a S5 K-sound reference voltage signal of less value than that of said S1 K-sound reference voltage level This is based upon the acknowledgement that, when taking the recurring pulsating sound due to heartbeats as a timing scale for identifying the Korotkoff sounds, S5 K-sound of less intensity than that of S1 K-sound can be accurately detected by comparison with a less reference level which is between the S1 K-sound level and the noise level even when the S5 K-sound has a level close to that lowered reference level That is, the incoming sound at a level above that lowered reference level can be identified as the Korotkoff sound only when it occurs in synchronism with the heartbeat, otherwise it can be regarded as the simple artifact noise. To this end, said S5 K-sound reference level is selected to be a value suitable for properly discriminating the desired Korotkoff or S5 K-sound. A comparator 54 serves to compare the input analog signal C from the absolute value amplifier 30 with thus determined S5 K-sound reference level in such a way that when the input signal C has a level above the reference level it provides a high level output voltage, which is in turn fed through a voltage adjusting circuit 55 to a monostable multivibrator 56. The multivibrator 56, in response to the high level input, provides a gate signal E having a pulse width of 100 milliseconds to be to one input of an AND gate 57. Applied to the other input of the AND gate 57 is a signal F transmitted from a heartbeat detecting section 120. Said heartbeat detecting section 120 comprises a low-pass filter, a comparator and a monostable multivibrator (all not snown) arranged to provide an output representative of each heartbeat during the measurement. The low-pass filter serves to suppress the frequency components below 10 Hz of the incoming signal A from said sound detecting section 6 so as to pass the signal including pulsating sounds due to the heartbeats. The comparator is introduced to provide an output as a result of the comparison or the incoming signal A with a predetermined heartbear reference level for identification of each heartbeat, such output representative of each heartbeat triggering the multivibrator so as to issue the above signal F at a high voltage level which is the input of said AND gate 57 of the S5 K-sound discriminating section 50. With the result of this, the AND gate 57 provides a high level voltage signal G only when the comparator 54 sees a signal of the amplitude above the S5 K-sound reference level during a time period in which the heartbeat occurs Consequently, the signal G at the high level can be recognized as representing the detection of the Korotkoff sound including S5 K-sound. Final identification of S5 K-sound is made in the subsequent stage of said K-sound evaluating section 80.

Figure 9:
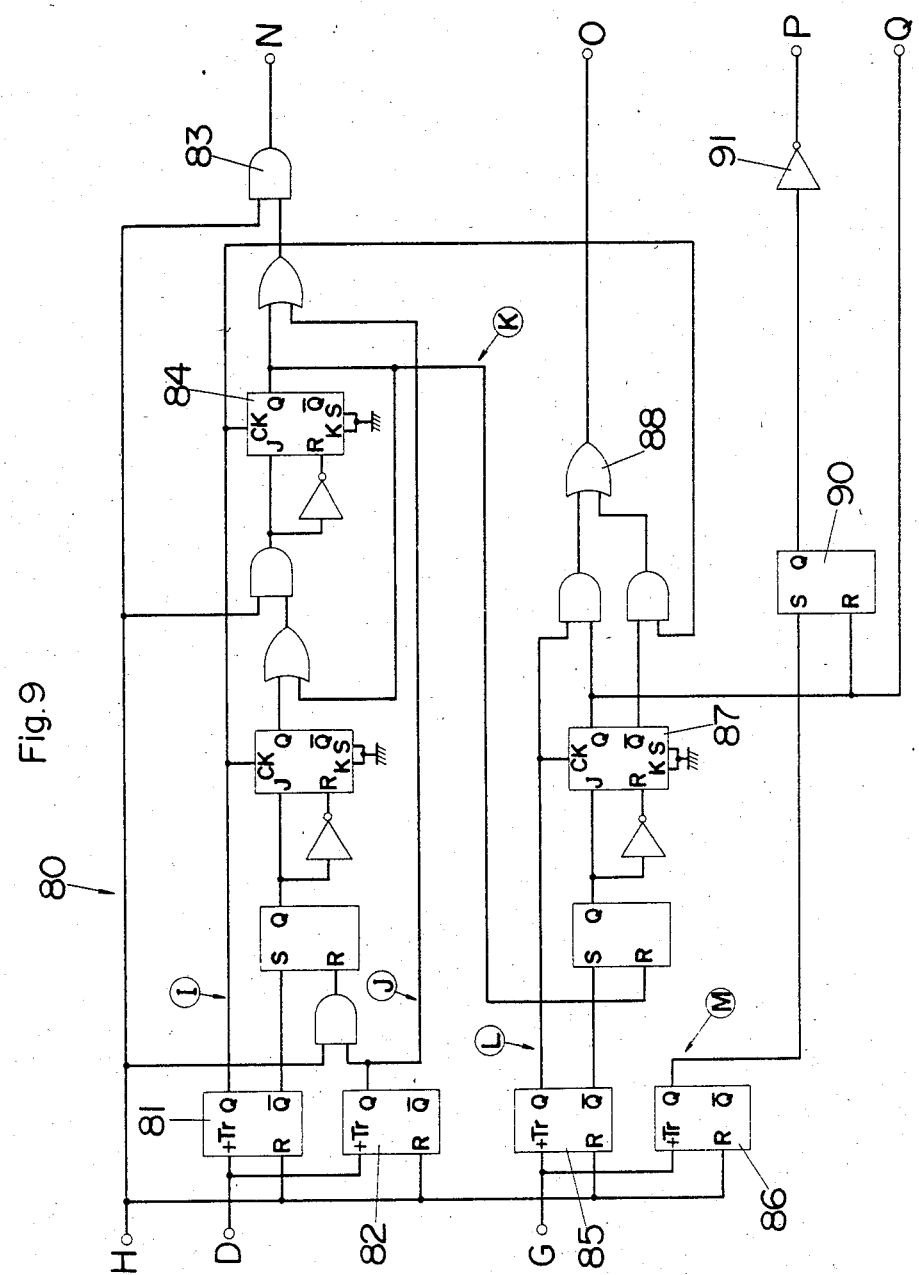
FIG. 9 is a block diagram showing a Korotkoff sound evaluating section employed in the above embodiment.

Now referring to FIG. 9, the K-sound evaluating section 80 has three input terminals respectively for the signal D from the S1 K-sound discriminating section 40, the signal G from the S5 K-sound discriminating section 50 and the signal H from a reset switch 95 which is arranged to normally provide the high level signal H and conversely to provide the low level signal H by being manually turned over, such low level signal H serving to reset the evaluating section 80 back to the initial condition as is required at the start of the measurement by this instrument or at the time when an unexpected noise induces the false operation of the instrument. Four kinds of operations can be effected with this circuit arrangement of the K-sound evaluating section 80.

Firstly, the identification of S1 K-sound among the incoming signals D from the S1 K-sound discrimination section 40 is attained by a first logic circuit beginning within a pair of monostable multivibrators 81 and 82 and ended with an AND gate 83. Such identification of S1 K-sound is achieved by a unique technique of counting the pulse numbers of the incoming signal D representative of the Korotkoff sounds and possible noises at levels equivalent thereto during a predetermined time interval. This is based on the general acknowledgement that the Korotkoff sounds will appear in synchronism with the heartbeats and therefore the Korotkoff sounds should appear successively at intervals no later than a limited value, for example, 2 to 4 seconds and that the several Korotkoff sounds or no less than three Korotkoff sounds should continuously appear. Consequently, the occurrence of the true Korotkoff sounds can be recognized only when the signal D from the S1 K-sound discriminating section 40 has gone high repeatedly at a time interval of 2 to 4 seconds at the same time it has gone high no less than three times. In other words, mere occurrences of high level states or the signal D at the time interval exceeding the above or only two times of such occurrence of the signal D can not be the indication of the true Korotkoff sounds. To this end, one multivibrator 81 is designed to provide a series of output pulses I, each having a pulse width of as little as 30 msec and beginning on each rising edge of the signal D, for representing the repetitions of high level states seen in the signal D, and the other multivibrator 82 provides a series of output pulses J, each having a pulse width of 2 to 4 sec and beginning on each rising edge of the signal D, for defining said limited time interval. It is to be noted at this point that the multivibrator 82 is a retriggerable one so that it will elongate an effective pulse width of its output J when the signal D repeats the high level states at a less time interval than the above. Other arrangement of the first logic circuit including several gates and flip-flops is such that the AND gate 83 is held in an initial condition for providing a low level output N until the circuit receives the signal D from the S1 K-sound discriminating section 40 and it is in condition for providing a high level output N each time the multivibrator 82 produces a high level output signal J in response to the signal D and that the AND gate 83 will continue to provide the high level output N after three or more high level states in the incoming signal D has been detected, in which the flip-flop 84 operates to count the times of occurrence that the signal D goes high and provide a low level output K until it has counted three times of such occurrence. Particularly worthy of mention among the functions of this circuit is that it becomes reset when the high level state of the signal D is not repeated within the pulse width of the output J, say 2 to 4 seconds before the flip-flop 84 has counted three times of occurrence of the signal D going high. The output signal N thus indicating the occurrence of the first and succeeding true Korotkoff sounds serves as S1 decisive signal which is applied to the control section 20 where it is processed so as to finally identify the S1 K-sound and the corresponding blood pressure with the help of other information to be applied thereto.

The second operation of the K-sound evaluating section 80 is to selectively pass therethrough the signals D and G respectively representative of S1 and S5 K-sounds as an output O in accordance with the result of the above first logic circuit, and this switching operation is effected by a second logic circuit operatively connected to the flip-flop 84 of the above first logic circuit and including a pair of monostable multivibrators 85 and 86, a flip-flop 87 and an OR gate 88. After the first logic circuit has seen three or more high level repetitions of the signal D in the elongated time interval, the flip-flop 87 of the second logic circuit is made ready for marking another succeeding or fourth occurrence of the high level state of the signal D. Upon recognition of four times of such occurrence in the signal D, the seecond logic circuit is entered in condition for passing the signal G through said OR gate 88 as the output O, while it remains in condition for passing the signal D untl this occurrence. Said multivibrators 85 and 86 are designed to provide output pulses of 30 milliseconds and 2 to 4 seconds width respectively when triggered on the rising edge of each pulse of the signal G. The third operation of the K-sound evaluating section 80 is to present a S5 K-sound decisive output P after a third logic circuit including the above flip-flop 87, a monostable multivibrator 90 and a NOT gate 91 have counted five times the occurrences of the high level state of the signal D after the acknowledgement of the three successive high level repetitions of the signal D during said elongated time interval by the first logic circuit. Such S5 K-sound decisive signal P issued from the NOT gate 91 is therefore the indication of the appearance of S5 K-sound when going high and is to inform that fact to the subsequent control section 20. The fourth operation of the K-sound evaluating section 80 is to provide a S1–S5 switching signal Q only after the true K-sounds is counted four times, such switching signal Q being the output of the above flip-flop 87 and indicating whether said output signal O is representative of S1 K-sound or S5 K-sound. These output signals N, O, P and Q from the K-sound evaluating section 80 are all fed to the next control section 20 where they are processed so as to determine the S1 and S5 K-sounds along with the corresponding blood pressures. These blood pressure indications are represented in digital representation on the display section 21 under the operarion of the control section 20.

Figure 8:
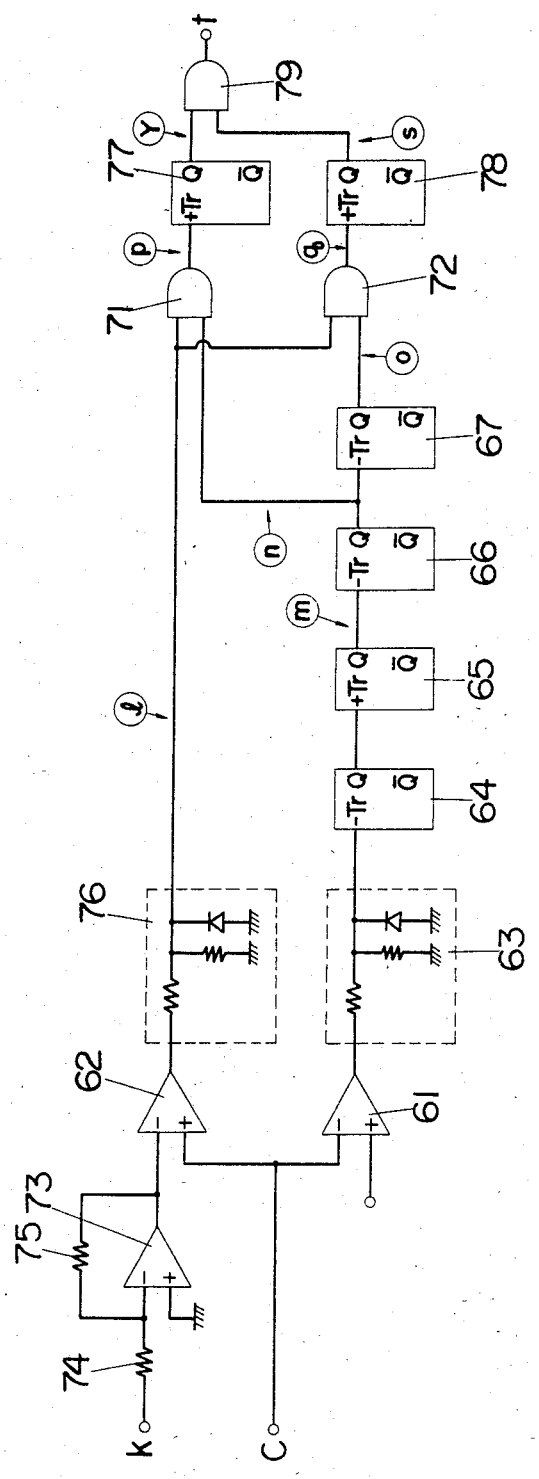
FIG. 8 is a block diagram showing a voiced tone discriminating section employed in the above embodiment.

Reference is now made to a voice tone discriminating section 60 which has an advantageous function of judging whether the measurement by the instrument is being performed on the basis of a voiced tone. It is known in the blood pressure measurement by the doctors or like skilled personnel who rely on the ear that the measurement can be judged to be correct and accurare when the first to fourth phases of Korotkoff sounds proposed by Swan appears regularly and successively without the lack of any one of the phases as well as that the voiced rone can be heard in the second phase of Korotkoff sounds in the regular succession of the phases I through IV. From this, the voiced tone can serve as a suitable and strong reference for judging whether the blood pressure measurement is being performed properly and correctly and this is the reason that the voiced tone discriminating section 60 is incorporated in the instrument of the present invention. As shown in FIG. 8, the voiced tone discriminating section 60 includes a first comparator 61 for receiving the analog signals C from said absolute value amplifier section 30. At the first comparator 61 the amplitude of the signal C is compared with a first K-sound reference level which is set to be slightly above said S1 K-sound reference level and be equivalent to 65 to 70 dB in tne normal listening level of human ear. By this comparison, a high level output from the comparator 61 is given when the signal C representative of the amplitude of the sound sensed by the microphone has a larger value than said first K-sound reference value, indicating that the signal C is in such a larger level that the sensed sound can be expected to include the voiced tone. The output of the first comparator 61 is fed through a voltage adjusting circuit 63 to a series of multivibrators 64 th ough 67 so as to sequentially trigger them to provide first and second gate signals (n) and (o) respectively being the inputs of first and second AND gates 71 and 72. Prior to discussing the meanings of the gate signals, it should be noted that the voiced tone in question normally appears within a certain time period immediately after the occurrence of the particular K-sound and that the voiced tone results from continuous signals of rather less amplitude. The present embodiment implements the abov facts by employing a gating technique which discriminates the voiced tone in such a manner as to examine whether or not a signal having a voltage level enough to be expected to be representative of the voice tone appears within the predetermined time period or periods after the detection of the signal representative of the K-sound, the level of which is of course higher than that of the signal ror voiced tone. In the present embodiment, two successive time periods during each of which the above discrimination can be effected, are utilized for more accurate discrimination. The first and second gate signals (n) and (o) are delayed signals which have the same pulse width of 40 to 60 msec but begin respectively 50 msec and 90 msec after the rising edge of the output from the comparator 61 for defining respectively the above time periods for the voiced tone discrimination. The above timing operation is due to the combination of multivibrator 64 responding to the rising edge of the input from comparator 61 for providing an output pulse of 100 msec width, multivibrator 65 responding to the rising edge of the input for providing an output pulse of 50 msec width, multivibrator 66 responding to the falling edge of the input for providing an output pulse of 40 to 60 msec width which is said first gate signal (n), and multivibrator 67 responding to the falling edge of the input for providing an output pulse of 40 to 60 msec width which is said second gate signal (o). An operational amplifier 73 forms with a pair of resistors 74 and 75 of suitable values a constant-gain multiplier providing a second K-sound reference voltage level (voiced tone reference level) which is below said S1 K-sound level for properly identifying the occurrence of the voiced tone. The second K-sound reference level is fed to a second comparator 62 which compares the analog signal C from the absolute value section 30 therewith to issue an output pulse when the signal C exceeds the voiced tone reference level, such output (1) being fed through a voltage adjusting circuit 76 to each of said first and second AND gate 71 and 72 as high level inputs. It is at this time that the discrimination of the voice tone is performed in such a way that the first AND gate 71 provides a high level output (p) which is the indication of the true voiced tone appearing in said predetermined time interval defined by the first gate signal (n) as well as that the second AND gate 72 provides a high level output(q) which is the indication of the true voiced tone appearing in the next time interval defined by the second gate signal (o). The outputs (p) and (q) are applied to respective monostable multivibrators 77 and 78 where they undergo wave-shapings for timing matching purpose and thereafter applied to a third AND gate 79, which provides a high level output (t) only when the voiced tone appears both in said discrete time intervals defined by the first and second gate signal (n) and (o). The output (t) is then fed to said control circuit 20, which in response to the output (t) going high actuates a voiced tone indication lamp (not shown) in the display section 21 to light up during a preselected time period, indicating that the on-going blood pressure measurement is available. Consequently, the user is informed that the measurement is being performed erroneously in the absence of lighting up of the lamp with the result that he or she is required to rest the instrument for another measurement.

Figure 10:
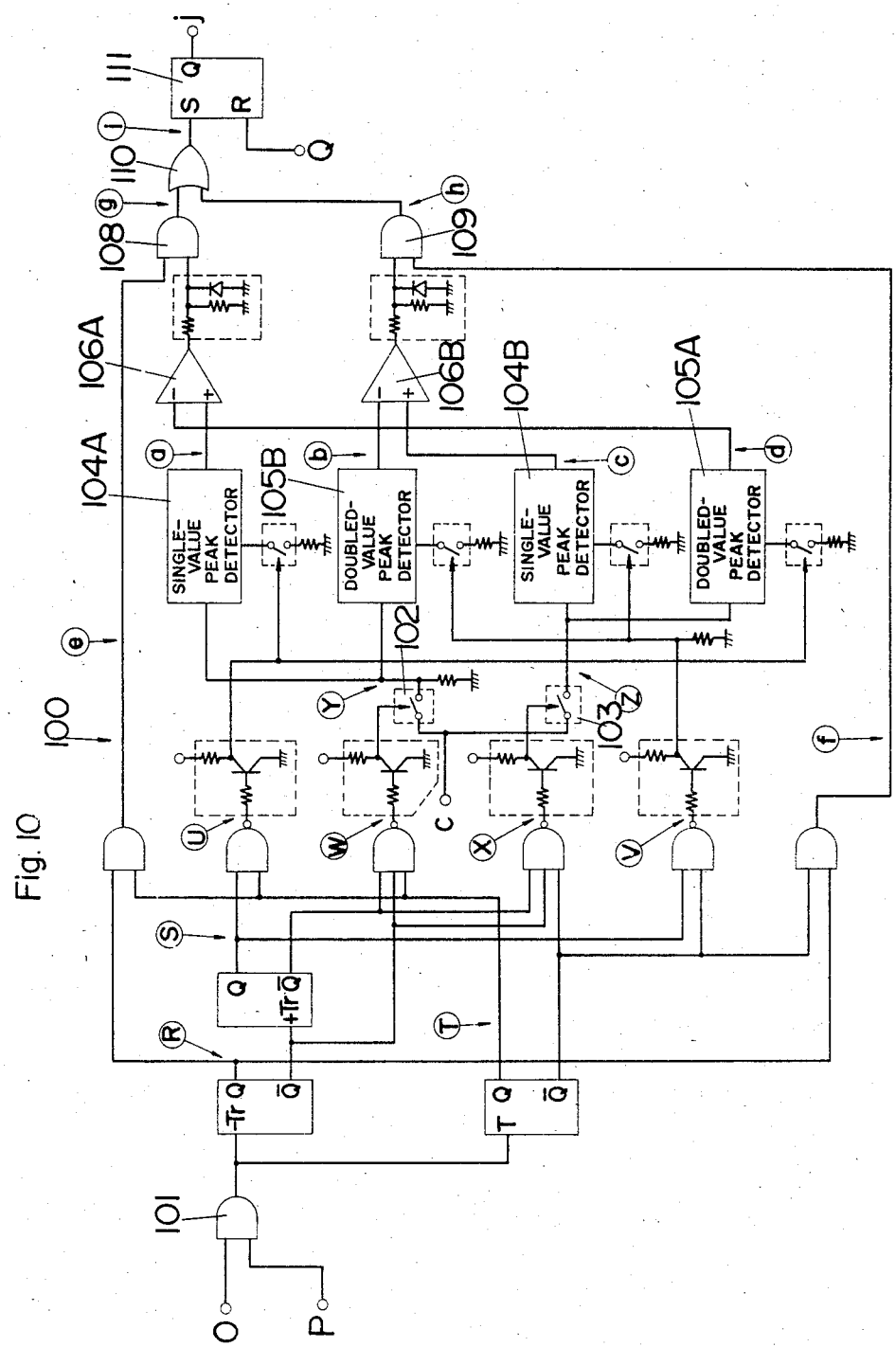
FIG. 10 is a block diagram of a S4 Korotkoff sound discriminating section employed in the above embodiment.
Figure 11A:
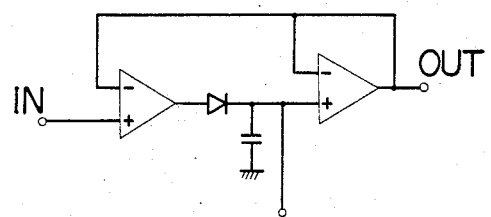
FIGS. 11(A) and 11(B) are respectivele circuit diagrams of a single-value peak detector and a doubled-value peak detector utilized in the section of FIG. 10.
Figure 11B:
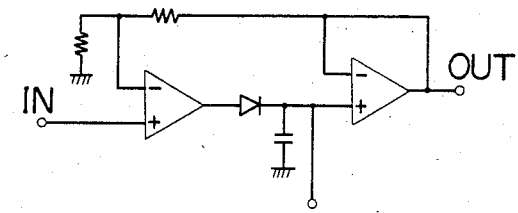
Figure 12:
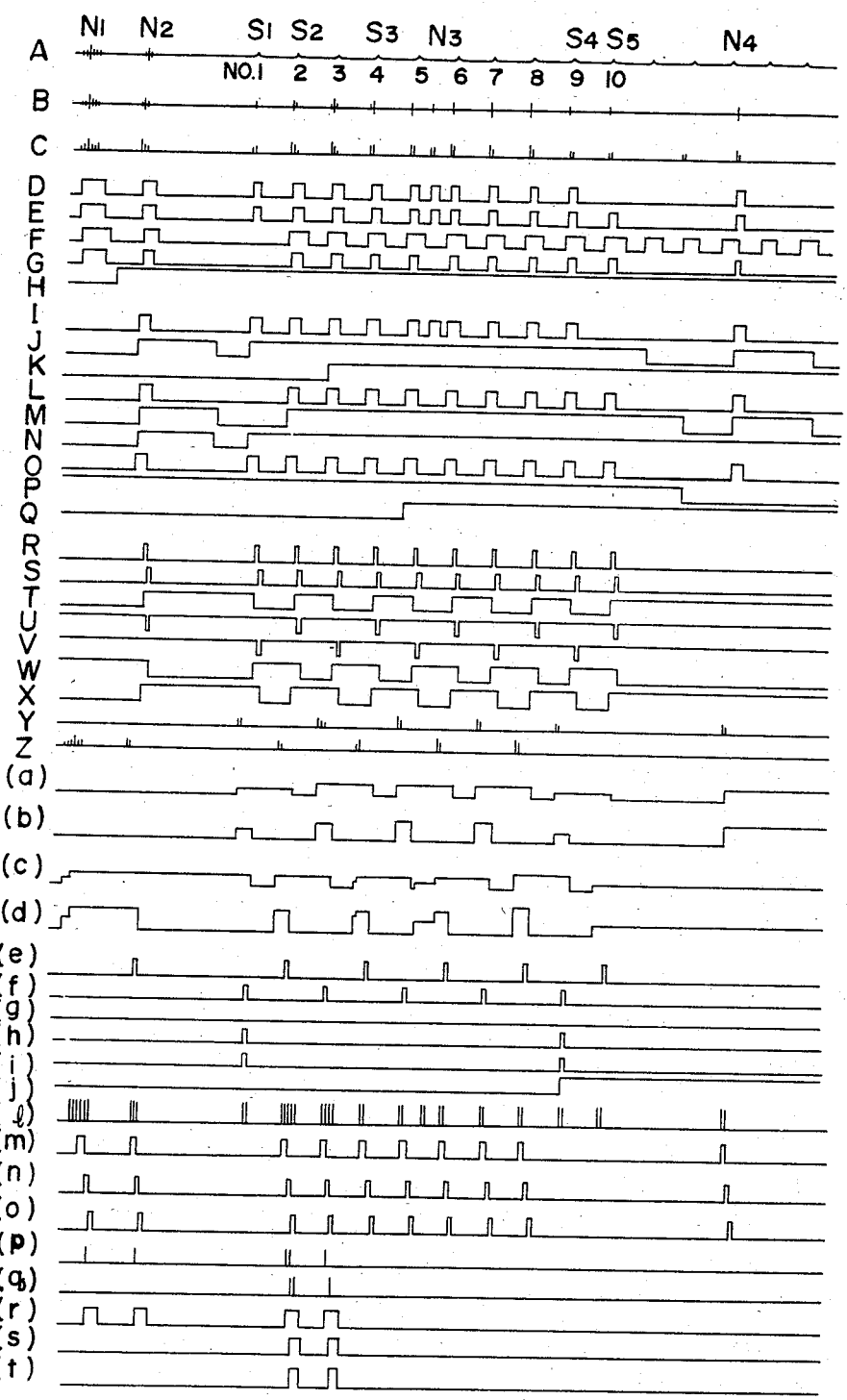
FIG. 12 is graphic representation of time related signal waveforms showing the time variant voitages at the corresponding points in several figures.

Referring to FIG. 10, there is shown the circuit diagram of a S4 K-sound discriminating section 100 which cooperates with said absolute value amplifier section 30 and K-sound evaluating section 80 to discriminate the S4 K-sound which is in some cases required for determining a diastolic pressure instead of S5 K-sound or along with S5 K-sound. The analysis of the S4 K-sound proved that it can be defined as a particular Korotkoff sound whose peak value is about a half that of the preceding Korotkoff sound in a normal listening level of the human ear. The S4 K-sound discriminating section 100 is operated based upon this definition so as to discriminate a signal representative of the S4 K-sound among the incoming signals C from said absolute value amplifier section 30. In operation, said signals O and P from the K-sound evaluating section 80 are utilized as a timing scale for comparison of any combination of two succeeding signals C. The output signals O and P are applied to an AND gate 101 so that the above comparison can be performed each time when the signal O goes high to indicate the occurrence of the Korotkoff sounds until said S5 K-sound decisive signal P goes low to indicate that the S5 K-sound has been detected. The circuit arrangement of the S4 K-sound discriminating section 100 is basically composed of two identical sub-circuits, one for comparison with respect to peak value between the signal C appearing in odd numbers and nextly appearing signal C, and the other between the signal C appearing in even numbers and nextly appearing signal C. For example, when referring to subscript numbers (1, 2, . . . 10) corresponding to the Korotkoff sounds and their amount of intensity indicated respectively at A and C of FIG. 12, one of the above sub-circuits is responsible for the comparison between signals no. 1 and no. 2, no. 3 and no. 4, and so on, while the other sub-circuit is responsible for the comparison between signals between no. 2 and no. 3, no. 4 and no. 5, and so on. Common to the sub-circuits are a pair of analog gates 102 and 103 which receives respective analog signals C so as to produce respective outputs which are the function of the corresponding input signals C in accordance with respective timing pulses to be input thereto. Included in each of the sub-circuits are a single-value peak detector 104A (104B) which holds a value of the highest input signal value and a doubled-value peak detector 105A (105B) which holds a doubled value of the highest input signal. A comparator 106A (106B) is connected to each combination of the single-value peak detector 104A (104B) and the doubled-value peak detector 105A (105B) to compare any combination of two adjacent signals in such a way as to discriminate the S4 K-sound. When the preceding one of any combination of two successive signals C has a greater peak value than the following one, the comparator 106A (106B) provides a low level output which is the indication of not having detected the S4 K-sound, and when the preceding one of any combination of two successive signals C has a peak value not greater than the following one, the comparator 106A (106B) provides a high level output which is the indication of having detected the S4 K-sound. The outputs from the comparators 106A and 106B are verified at respective AND gates 108 and 109 and then fed to an OR gate 110 so as to provide a corresponding high level output representative of the S4 K-sound when either of two comparators 106A and 106B provides a high level output. Also included in the S4 K-sound discriminating section 100 is a latching flip-flop 111 which is in a locked state by the S1-S5 switching signal Q to provide a low level output (j) irrespective of the output from the OR gate 110 until the signal Q goes high, and which is in set state after the signal Q goes high so as to provide a high level output or S4 K-sound decisive signal (j) in response to the high level output from the OR gate 110. Consequently, the S4 K-sound discriminating section 100 will not operate until the signal Q goes high or until the S5 K-sound is detected. This results from the understanding that S4 K-sound will not appear any sooner than five times of occurrence of the Korotkoff sounds in the normal blood measuring condition. It is, of course, known that other means may be incorporated in the above circuit to enable the flip-flop 111 until the Korotkoff sounds are detected predetermined times instead of the S1-S5 switching signal Q. Waveforms of a number of signals at portions in the circuit of FIG. 10 are shown in FIG. 12 for easy understanding of the operation of the above S4 K-sound discriminating section 100 and the detailed circuitries of the above single-value and double-value peak detectors are respectively shown in FIGS. 11(A) and 11(B). It is noted at this point that FIG. 12 shows the state in which no. 9 K-sound is identified as the S4 K-sound after successfully rejecting noises and other K-sounds which might otherwise be the S4 K-sound by mistake.

At the control section 20, the ever decreasing pressure values within the cuff 2 sensed by the pressure transducer 18 and converted into the corresponding digital indication is initially controlled to be indicated respectively at S1 systolic pressure, S4 diastolic pressure and S5 diastolic pressure indication segments (not shown) on the display section 21 while the S1 K-sound decisive signal N is at low level. When the signal N firstly goes high to be representative of S1 K-sound, S5 K-sound or other possible noises of equivalent level thereto, the control section 20 operates to hold the pressure value at this moment at said S1 systolic pressure indication segment while to leave the pressure values at other segments to decrease. Subsequently, if the control section 20 sees that the signal N goes low, the above pressure indications are canceled and ever decreasing pressure values appear again at the S1 systolic pressure indication segment until the signal N goes high at which the instantaneous pressure value is held at the indication segment as in the above. In the following course of the measurement, the moment when the S4 K-sound decisive signal (j) goes high a particular pressure value at this moment is held at S4 diastolic pressure indication segment, such pressure value thus held corresponding to the occurrence of no. 9 K-sounds shown in FIG. 12. Further, when the S5 K-sound decisive signal P goes high to be representative of S5 K-sound the instantaneous pressure value at this moment is held at the S5 diastolic pressure indication segment, such pressure value corresponding to the occurrence of no. 10 K-sound shown in FIG. 12. During the above operation, the control section 20 actuates the voiced tone indication lamp in the display section 21 to light up during the preselected time period upon the occurrence of the signal (t) from the voiced tone discriminating section 60 going high to represent the detection of the voiced tone, notifying the user that the measurement is being successfully performed. Warning means may be incorporated in the instrument of the present invention for issuing a warning signal when no voiced tone is detected during a predetermined time interval in which it can be expected to appear in the proper blood pressure measurement, warning the user that the measurement being performed is no more effective. Finally, when the S5 K-sound decisive signal P goes low, the control section 20 decides the completion of the measurement and holds the pressure indications at all indication segment at the same time inform the user of the completion such as by lighting up a lamp or by issuing a beep. The above pressure indications can be held until said reset switch 95 is pressed for making the instrument ready for next measurement.

In the meanwhile, the output A emitted from the sound detecting section 6 is fed to a headphone driver 130 connected to headphones 131 which can be used for training personnel for discriminating the Korotkoff sounds. Also, the output A can be recorded on a data recorder (not shown) for repeated training of the above Korotkoff sound discrimination.

Although the present invention has been described in its preferred embodiment, it should be understood by those skilled in the art that the present invention is not limited to the present embodiment and various changes and modifications may be made without departing the spirit and scope of the present invention.

What is claimed is:

1. An automated blood pressure monitoring instrument comprising:
means for externally occluding an artery with pressure;
transducer means responding to sounds including Korotkoff sounds emitted from the occluded artery for generating electric signals representative thereof;
filter means which receives the output signals from the transducer means to allow only the signals within a frequency range in the vicinity of the frequencies inherent to the Korotkoff sounds to pass as analog signals indicative of the intensities of the sounds sensed;
noise level detecting means which receives from said filter means the signals of different levels to calculate a noise level therefrom in such a manner as to exclude from said calculated noise level, expected levels which suggest the Korotkoff sounds and the like and which are higher than an estimated or assumed level of artifact noises emanating from the occluded artery and the body;
comparator means which successively receives the incoming signals from the filter means to compare their levels with a Korotkoff sound reference level which is defined to be proportional to said noise level determined and to be thereabove such that it provides a Korotkoff signal representative of the Korotkoff sound each time when the incoming signal is judged to have a greater level than the Korotkoff sound reference level; and
display means responding to the appearance and disappearance of the Korotkoff sound signal for providing blood pressure indications wherein said transducer means comprises a stethoscope with a pressure sensing pad adapted to be placed on the human body adjacent to the occluded artery, a microphone mounted within an ear plug of the stethoscope, a microphone sensitivity compensating filter means for providing a generally flat frequency response, and a frequency weighting filter means for adjusting the output from the microphone sensitivity compensating filter to an equal loudness contour which is characteristic to the human.

2. The automated blood pressure monitoring instrument as set forth in claim 2, wherein said frequency weighting filter means is a filter having the reverse characteristic of the 60-phon equal loudness contours such that the output of frequency weighting filter means provides a frequency characteristic approximating that loudness contour.

3. The automated blood pressure monitoring instrument as set forth in claim 2, wherein said stethoscope is provided at its ear plugs respectively with extension tubes each of which is designed to have generally the same length as that of the external auditory canal of the human ear and wherein a bypass tube is interconnected between the extension tubes for intercommunication therebetween to define together with said extension tubes an artificial ear analogous to the human ear, said microphone being received within one extension tube at the outer extremity thereof to be located outwardly of the connecting point between that extension tube and said bypass tube, and the other extension tube being closed at its outer extremity.

4. The automatic blood pressure monitoring instrument as set forth in claim 1, wherein said noise level detecting means comprises:
an absolute value amplifier means which receives the signals from the filter means to amplify the values thereof both positive and negative with respect to a base level for providing corresponding analog signals indicating the intensities of the sound sensed;

a clipper-limiter means of which critical level is set to be a highest value among the expected values of the artifact noises appearing in the normal blood pressure measuring condition for providing a corresponding output which is the function of the signal from said amplifier for that signal having a level below said critical level and providing an output at such critical level for that signal from the amplifier having level thereabove;

an averaging circuit responding to the outputs from said clipper-limiter means for providing a mean level defining said noise level indicative of the level of the artifact noises peculiar to the person under blood pressure measurement, whereby the level of each signal from the absolute value amplifier means is subsequently compared at said comparator means with said Korotkoff sound reference level for discrimination of the true Korotkoff sound.

5. The automated blood pressure monitoring instrument as set forth in claim 1 including voiced tone discriminating means for discriminating a voiced tone associated with a particular Korotkoff sound among the successively appearing Korotkoff sounds and including notifying means which provides indication upon the recognition of the voiced tone, said voiced tone discriminating means comprising:

first comparator means for comparison of the levels of the analog signals fed from said filter means with a first predetermined reference level set to be above said noise level in such a way as to provide a monitoring signal each time when the analog signal from the filter means exceeds said first reference level to indicate the Korotkoff sound which may be accompanied by the voiced tone;

recognition means responding to the monitoring signal for providing a recognition signal indicative of the appearance of the voice tone when it recognizes during a preselected time period within which the voiced tone is expected to appear subsequent to the associated Korotkoff sound that the level of the analog signal from the filter means exceeds a voiced tone reference level which is above said noise level but below said Korotkoff sound reference level for discriminating the voiced tone from the artifact noises.

6. The automated blood pressure monitoring instrument as set forth in claim 5, wherein said recognition means further comprises:

gate signal generating means responding to the monitoring signal for generating a gate signal during a preselected time period which begins on a predetermined time interval after the rising edge of said monitoring signal;

second comparator means for comparison of the level of the analog signal from the filter means with said voiced tone reference level to produce an output signal when the former exceeds the latter; and a gate having input terminals respectively for said gate signal and output signal from the second comparator means and arranged to produce said recognition signal only when the two signals are logically coincident with one another.

7. The automated blood pressure monitoring instrument as set forth in claim 5, wherein said recognition means further comprises:

gate signal generating means responding to the monitoring signal for generating a first gate signal during a first preselected time period which begins at a predetermined time interval after the rinsing edge of the monitoring signal and for generating a second gate signal during a second preselected time period which begins at the falling edge of said first gate signal;

second comparator means for comparison of the level of the analog signal from the filter means with said voiced tone reference level to produce an output signal when the former exceeds the latter;

a first gate having input terminals respectively for said first gate signal and output signal from the second comparator means and arranged to produce a first recognition signal only when the two signals are logically coincident with one another;

a second gate having input terminals respectively for said second gate signal and output signal from the second comparator means and arranged to produce a second recognition signal only when the two signals are logically coincident with one another;

wave elongating means for matching the timing of the first and second recognition signals for logical comparison therebetween; and a third gate having input terminals provided for the above comparison between the first and second recognition signals and arranged to produce a final recognition signal responsible for accurate identification of said voiced tone when the two signals are logically coincident with one another.

8. An automated blood pressure monitoring instrument comprising:

means for externally occluding an artery with pressure;

transducer means responding to sounds including Korotkoff sounds emitted from the occluded artery for generating electric signals representative thereof;

filter means which receives the output signals from the transducer means to allow only the signals within a frequency range in the vicinity of the frequencies inherent to the Korotkoff sounds to pass as analog signals indicative of the intensities of the sounds sensed;

noised level detecting means which receives from said filter means the signals of different levels to calculate a noise level therefrom in such a manner as to exclude from said calculated noise level, expected levels which suggest the Korotkoff sounds and the like and which are higher than an estimated or assumed level of artifact noises emanating from the occluded artery and the body;

comparator means which successively receives the incoming signals from the filter means to compare their levels with a Korotkoff sound reference level which is defined to be proportional to said noise level determined and to be thereabove such that it provides a Korotkoff signal representative of the Korotkoff sound each time when the incoming signal is judged to have a greater level than the Korotkoff sound reference level; and display means responding to the appearance and disappearance of the Korotkoff sound signal for providing blood pressure indications, wherein said noise level detecting means comprises:

an absolute value amplifier means which receives the signals from the filter means to amplify the values thereof both positive and negative with respect to a base level for providing corresponding analog signals indicating the intensities of the sound sensed;

a clipper-limiter means of which critical level is set to be a highest value among the expected values of the artifact noises appearing in the normal blood pressure measuring condition for providing a corresponding output which is the function of the signal from said amplifier for that signal having a level below said critical level and providing an output at such critical level for that signal from the amplifier having a level thereabove;

an averaging circuit responding to the outputs from said clipper-limiter means for providing a mean level defining said noise level indicative of the level of the artifact noises peculiar to the person under blood pressure measurement, whereby the level of each signal from the absolute value amplifier means is subsequently compared at said comparator means with said Korotkoff sound reference level for discrimination of the true Korotkoff sound.

9. An automated blood pressure monitoring instrument comprising:

means for externally occluding an artery with pressure;

transducer means responding to sounds including Korotkoff sounds emitted from the occluded artery for generating electric signals representative thereof;

filter means which receives the output signals from the transducer means to allow only the signals within a frequency range in the vicinity of the frequencies inherent to the Korotkoff sounds to pass as analog signals indicative of the intensities of the sounds sensed;

noise level detecting means which receives from said filter means the signals of different levels to calculate a noise level therefrom in such a manner as to exclude from said calculated noise level, expected levels which suggest the Korotkoff sounds and the like and which are higher than an estimated or assumed level of artifact noises emanating from the occluded artery and the body;

comparator means which successively receives the incoming signals from the filter means to compare their levels with a Korotkoff sound reference level which is defined to be proportional to said noise level determined and to be thereabove such that it provides a Korotkoff signal representative of the Korotkoff sound each time when the incoming signal is judged to have a greater level than the Korotkoff sound reference level; and display means responding to the appearance and disappearance of the Korotkoff sound signal for providing blood pressure indications, including voiced tone discriminating means for discriminating a voiced tone associated with a particular Korotkoff sound among the successively appearing Korotkoff sounds and including notifying means which provides indication upon the recognition of the voiced tone, said voiced tone discriminating means comprising:

first comparator means for comparison of the levels of the analog signals fed from said filter means with a first predetermined reference level set to be above said noise level in such a way as to provide a monitoring signal each time when the analog signal from the filter means exceeds said first reference level to indicate the Korotkoff sound which may be accompanied by the voiced tone;

recognition means responding to the monitoring signal for providing a recognition signal indicative of the appearance of the voiced tone when it recognizes during a preselected time period within which the voiced tone is expected to appear subsequent to the associated Korotkoff sound that the level of the analog signal from the filter means exceeds a voiced tone reference level which is above said noise level but below said Korotkoff sound reference level for discriminating the voiced tone from the artifact noises.

10. The automated blood pressure monitoring instrument as set forth in claim 9, wherein said recognition means further comprises:

gate signal generating means responding to the monitoring signal for generating a gate signal during a preselected time period which begins on a predetermined time interval after the rising edge of said monitoring signal;

second comparator means for comparison of the level of the analog signal from the filter means with said voiced tone reference level to produce an output signal when the former exceeds the latter, and a gate having input terminals respectively for said gate signal and output signal from the second comparator means and arranged to produce said recognition signal only when the two signals are logically coincident with one another.

11. The automated blood pressure monitoring instrument as set forth in claim 6, wherein said recognition means further comprises:

gate signal generating means responding to the monitoring signal for generating a first gate signal during a first preselected time period which begins at a predetermined time interval after the rinsing edge of the monitoring signal and for generating a second gate signal during a second preselected time period which begins at the falling edge of said first gate signal;

second comparator means for comparison of the level of the analog signal from the filter means with said voiced tone reference level to produce an output signal when the former exceeds the latter, a first gate having input terminals respectively for said first gate signal and output signal from the second comparator means and arranged to produce a first recognition signal only when the two signals are logically coincident with one another;

a second gate having input terminals respectively for said second gate signal and output signal from the second comparator means and arranged to produce a second recognition signal only when the two signals are logically coincident with one another;

wave elongating means for matching the timing of the first and second recognition signals for logical comparison therebetween; and a third gate having input terminals provided for the above comparison between the first and second recognition signals and arranged to produce a final recognition signal responsible for accurate identification of said voiced tone when the two signals are logically coincident with one another.

* * * * *